(12) United States Patent
Schulte et al.

(10) Patent No.: US 7,199,274 B2
(45) Date of Patent: Apr. 3, 2007

(54) PREPARATION OF SUBSTITUTED INDENES

(75) Inventors: Jörg Schulte, Frankfurt (DE); Jörg Schottek, Frankfurt (DE); Lothar Fisch, Kelkheim (DE)

(73) Assignee: Basell Polyolefine GmbH, Wesseling (DE)

( * ) Notice: Subject to any disclaimer, the term of this patent is extended or adjusted under 35 U.S.C. 154(b) by 145 days.

(21) Appl. No.: 10/532,284

(22) PCT Filed: Oct. 18, 2003

(86) PCT No.: PCT/EP03/11585

§ 371 (c)(1),
(2), (4) Date: Apr. 21, 2005

(87) PCT Pub. No.: WO2004/037756

PCT Pub. Date: May 6, 2004

(65) Prior Publication Data

US 2005/0256344 A1 Nov. 17, 2005

Related U.S. Application Data

(60) Provisional application No. 60/425,445, filed on Nov. 12, 2002.

(30) Foreign Application Priority Data

Oct. 22, 2002 (DE) ................................ 102 49 325

(51) Int. Cl.
*C07C 13/36* (2006.01)
*C07C 13/32* (2006.01)
*C07C 13/28* (2006.01)

(52) U.S. Cl. ...................... 585/410; 585/415; 585/400; 585/435; 585/436

(58) Field of Classification Search ................ 585/400, 585/410, 415, 435, 536
See application file for complete search history.

(56) References Cited

U.S. PATENT DOCUMENTS

| 5,723,640 A | 3/1998 | Fukuoka et al. |
| 5,770,753 A | 6/1998 | Küber et al. |
| 5,789,634 A | 8/1998 | Sullivan et al. |

FOREIGN PATENT DOCUMENTS

WO WO-98/40331 9/1998

OTHER PUBLICATIONS

Holm, Torkil, "Thermochemical Bond Dissociation Energies of Carbon-Magnesium Bonds", J. Chem.Soc. Perkin Trans.2, 1981, pp. 464-467.

Ikoma, Yoshiharu et al., "Non-ligated Nickel Chloride-Catalyzed Cross-Coupling of Aromatic Grignard Reagents with Aryl Halides", Synthesis 1990, pp. 147-148.

Ellis, William W. et al., "Synthesis, Structure, and Properties of Chiral Titanium and Zirconium Complexes Bearing Biaryl Strapped Substituted Cyclopentadienyl Ligands", Organometallics 1993, vol. 12, pp. 4391-4401.

Witte, Peter et al., "Synthesis of Unbridged Bis(2-R-indenyl)zirconocenes Containing Functional Groups and Investigations in Propylene Polymerization", Organometallics 1999, vol. 18, pp. 4147-4155.

Beilstein Online, Registry No. 6314119, BE618638, XP002270402, 1994 and 1962, respectivley.

*Primary Examiner*—Elvis O. Price

(57) ABSTRACT

The present invention relates to a simple process for preparing specifically substituted indenes of the formula (I) or (Ia)

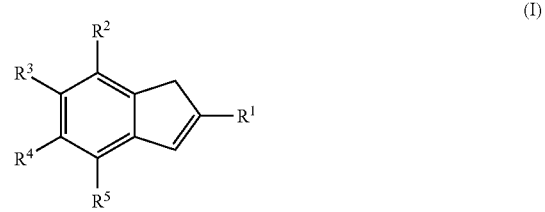

(I)

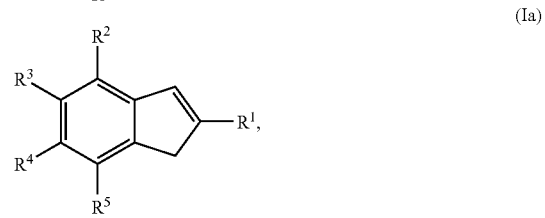

(Ia)

to compounds of the formula (II) serving as starting materials

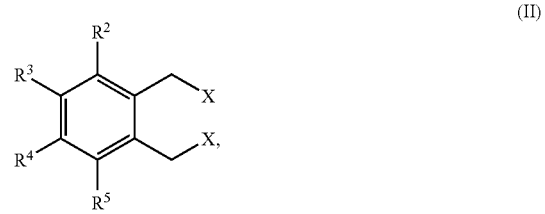

(II)

and to the use of the compounds of the formula (II) as starting materials for the synthesis of substituted indenes.

4 Claims, No Drawings

PREPARATION OF SUBSTITUTED INDENES

RELATED APPLICATIONS

This application is a national stage application (under 35 U.S.C. 371) of PCT/EP2003/022585 filed Oct. 18, 2003 which claims benefit to German application 102 49 325.1 filed Oct. 22, 2002 and U.S. provisional application 60/425,445 filed Nov. 12, 2002.

The present invention relates to a simple and efficient process for preparing specifically substituted indenes of the formula (I) or their double bond isomers of the formula (Ia)

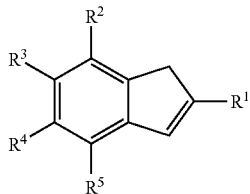

(I)

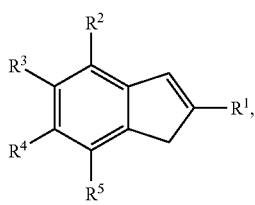

(Ia)

to compounds of the formula (II) serving as starting materials

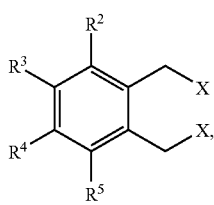

(II)

where $R^1$ is a $C_1$–$C_{40}$-hydrocarbon radical, $R^2$ is a substituted or unsubstituted $C_6$–$C_{40}$-aryl radical, where the substituents of this aryl radical are hydrocarbon radicals which contain no hydrogen atoms in α positions relative to aromatic radicals or vinylic groups, $R^3$–$R^5$ are identical or different and are each hydrogen or a $C_1$–$C_{40}$-hydrocarbon radical which contains no hydrogen atoms in α positions relative to aromatic radicals or vinylic groups, or $R^2$ together with $R^3$ forms a cyclic system, and X is a halogen atom, and also to the use of the compound of the formula (II) as starting material for the synthesis of substituted indenes.

Substituted indenes are important intermediates for the preparation of active compounds in the fields of pharmacy (Negwer, VCH 1987, p. 1703 ff.), crop protection, fine chemicals, liquid crystals and metallocene catalysts for the polymerization of α-olefins (Chem. Rev. 2000, number 4).

Substituted indenes can be used to prepare chiral ansa-metallocenes which are of great importance as transition metal components of highly active catalysts for stereospecific olefin polymerization.

Variation of the ligand system, for example by substitution, enables the catalyst properties to be influenced in a targeted way. This makes it possible to alter the polymer yield, the molecular weight distribution, the tacticity and the melting point of the polymers to the desired degree (Chem. Rev. 2000, number 4). Bridged zirconocenes containing, as π ligands, indenyl radicals which bear the bridge in position 1, preferably a hydrocarbon radical, in particular an alkyl radical, in position 2 and a further hydrocarbon radical, in particular a substituted or unsubstituted aromatic, in position 4 have been found to be particularly highly active and stereoselective catalyst systems, as described in U.S. Pat. No. 5,770,753 and U.S. Pat. No. 5,723,640. The ligand systems used for these highly active metallocenes are prepared from the corresponding substituted indenes.

The costs of preparing the indenes required for the metallocene synthesis represent an important part of the total cost of the metallocene synthesis. Various processes for the preparation of 2-alkyl-4-aryl-substituted indenes have been described, for example in U.S. Pat. No. 5,770,753, U.S. Pat. No. 5,723,640, WO 98/40331 and U.S. Pat. No. 5,789,634. The aryl radical in the 4 position is generally introduced by means of an aryl-aryl coupling catalyzed by transition metals either immediately at the beginning of the synthetic sequence or only after the indanone or indenyl framework has been built up. In the abovementioned processes, the alkyl radical in the 2 position on the indenyl framework is always introduced before the 1-indanone system has been built up. Organometallics 1993, 12, 4391–4401, describes the synthesis of bisindenyl metallocenes which are bridged in the 2 position and are unsubstituted on the six-membered ring and in which the two indenyl ligands which are bridged in the 2 position are built up directly by reaction of the bis-Grignard of α,α-dichloro-o-xylene with an appropriate bridging reagent. Organometallics 1999, 18, 4147–4155, describes the synthesis of indenes which are substituted in the 2 position by bulky aryl radicals and are unsubstituted on the six-membered ring, likewise by reaction of the bis-Grignard of α,α-dichloro-o-xylene with an appropriately substituted methyl benzoate.

The syntheses known hitherto for preparing 2-alkyl-4-aryl- or 2-alkyl-7-aryl-substituted indenes with varying 2 position on the indenyl system of ansa-metallocenes and fixed substituents in the 4 or 7 position on the indenyl system are still too time-consuming and thus too costly.

It is an object of the present invention to find a simple, flexible, quick and inexpensive process for preparing substituted 2-alkyl-4-arylindenes or 2-alkyl-7-arylindenes which avoids the disadvantages of the known processes and allows, in particular, the radicals in the 2 position on the endenyl system to be varied in a simple manner.

We have found that this object is achieved by a process for preparing substituted indenes of the formula (I)

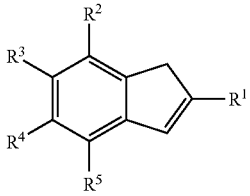

and their double bond isomers of the formula (Ia)

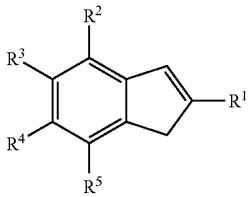

which comprises converting a compound of the formula (II)

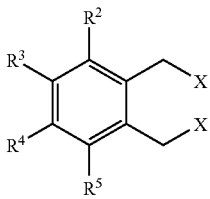

into a bisorganometallic compound of the formula (III)

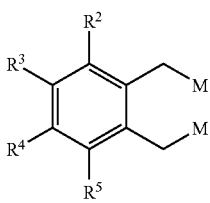

and reacting this with a compound of the formula (IV)

to give an indanol of the formula (V)

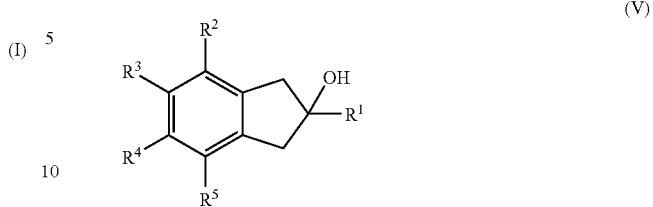

and converting this into an indene of the formula (I) or (Ia) by elimination of water,
where
$R^1$ is a $C_1$–$C_{40}$-hydrocarbon radical,
$R^2$ is a substituted or unsubstituted $C_6$–$C_{40}$-aryl radical, where the substituents of this aryl radical are hydrocarbon radicals which contain no hydrogen atoms in a positions relative to aromatic radicals or vinylic groups,
$R^3$–$R^5$ are identical or different and are each hydrogen or a $C_1$–$C_{40}$-hydrocarbon radical which contains no hydrogen atoms in a positions relative to aromatic radicals or vinylic groups, or $R^2$ and $R^3$ together form a cyclic system which contains no hydrogen atoms in a positions relative to aromatic radicals or vinylic groups, or $R^2$ together with $R^3$ forms a cyclic system,
X is a halogen atom,
M is lithium, sodium, potassium or magnesium monohalide or two radicals M together represent one magnesium atom, and
Y is a nucleophilic leading group.

Furthermore, we have found compounds of the formula (II)

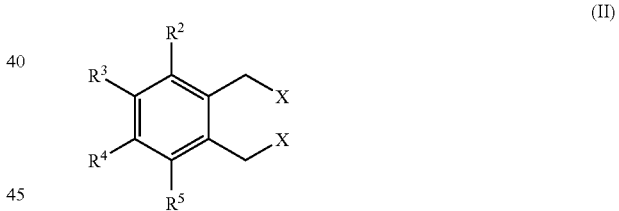

where $R^2$, $R^3$, $R^4$, $R^5$ and X are each as defined above, and also the use of these compounds as starting materials for the synthesis of substituted indenes.

$R^1$ is, for example, a $C_1$–$C_{20}$-alkyl radical, a $C_6$–$C_{18}$-aryl radical, a $C_7$–$C_{40}$-arylalkyl radical or a $C_7$–$C_{40}$-alkylaryl radical. $R^1$ is preferably a $C_1$–$C_{20}$-alkyl radical, in particular a linear, branched or cyclic $C_1$–$C_{10}$-alkyl radical.

$R^2$ is a substituted or unsubstituted $C_6$–$C_{40}$-aryl radical, where the substituents of this aryl radical are hydrocarbon radicals which contain no hydrogen atoms in a positions relative to aromatic radicals or vinylic groups. $R^2$ is preferably a substituted or unsubstituted $C_6$–$C_{18}$-aryl radical such as phenyl, 1-naphthyl, phenanthryl, 3-tert-butylphenyl, 4-tert-butylphenyl, 3,5-di(tert-butyl)phenyl, 4,4'-biphenyl or 3,5-di(phenyl)phenyl.

$R^3$–$R^5$ are identical or different and are each hydrogen or a $C_1$–$C_{40}$-hydrocarbon radical which contains no hydrogen atoms in a positions relative to aromatic radicals or vinylic groups. Examples of such hydrocarbon radicals are tert-butyl, tert-pentyl, 1-adamantyl, phenyl, 1-naphthyl, phenanthryl, 3-tert-butylphenyl, 4-tert-butylphenyl, 3,5-di(tert-butyl)phenyl, 4,4'-diphenyl and 3,5-di(phenyl)phenyl. $R^3$–$R^5$ are preferably hydrogen.

The radicals $R^2$ and $R^3$ may together form a cyclic system which contains no hydrogen atoms in a positions relative to aromatic radicals or vinylic groups, with $R^2$ and $R^3$ together with the atoms connecting them particularly preferably forming a substituted or unsubstituted 1,3-butadiene-1,4-diyl group. Particular preference is given to $R^2$ and $R^3$ together with the atoms connecting them forming an unsubstituted 1,3-butadiene-1,4-diyl group.

X is a halogen atom such as chlorine, bromine or iodine, and is preferably chlorine.

M is preferably magnesium monochloride.

Y is a nucleophilic leaving group such as halogen, an $R_6CO_2$ radical or an $OR^6$ radical. Y is preferably an $OR^6$ radical, where $R^6$ is a $C_1$–$C_{40}$-hydrocarbon radical such as a $C_1$–$C_{20}$-alkyl radical, a $C_6$–$C_{18}$-aryl radical, a $C_7$–$C_{40}$-arylalkyl radical or a $C_7$–$C_{40}$-alkylaryl radical. $R^6$ is preferably a $C_1$–$C_{10}$-alkyl radical.

Hydrogen atoms present in the a position relative to aromatic radicals or vinylic groups are, for example, benzylic hydrogen atoms as in the methyl group $(CH_3—C_6H_5)$ of toluene or in the methine group $((CH_3)_2CH—C_6H_5)$ of cumene or allylic hydrogen atoms as in the methylene group $(CH_2=CH—CH_2—CH_3)$ of 1-butene.

Unless restricted further, alkyl is a linear, branched or cyclic radical such as methyl, ethyl, n-propyl, isopropyl, n-butyl, i-butyl, s-butyl, t-butyl, n-pentyl, n-hexyl, cyclohexyl, n-heptyl or n-octyl.

The above-described process of the present invention is preferably used for preparing substituted indenes of the formula (I) or (Ia) in which $R^1$ is a linear, branched or cyclic $C_1$–$C_{10}$-alkyl radical, $R^2$ is a substituted or unsubstituted $C_6$–$C_{18}$-aryl radical selected from the group consisting of phenyl, 1-naphthyl, phenanthryl, 3-tert-butylphenyl, 4-tert-butylphenyl, 3,5-di(tert-butyl)phenyl, 4,4'-biphenyl and 3,5-di(phenyl)phenyl, $R^3$–$R^5$ are each hydrogen, X is a chlorine atom, M is magnesium monochloride and Y is $OR^6$, where $R^6$ is a linear, branched or cyclic $C_1$–$C_{10}$-alkyl radical.

In the preferred embodiment, the radicals and substituents can be described in more detail as follows:

$R^1$ is a linear, branched or cyclic $C_1$–$C_{10}$-alkyl radical. Examples of radicals $R^1$ are methyl, ethyl, n-propyl, isopropyl, n-butyl, sec-butyl, isobutyl, n-pentyl, cyclopentyl, n-hexyl, cyclohexyl, n-heptyl, n-octyl and n-decyl.

$R^2$ is a substituted or unsubstituted $C_6$–$C_{18}$-aryl radical selected from the group consisting of phenyl, 1-naphthyl, phenanthryl, 3-tert-butylphenyl, 4-tert-butylphenyl, 3,5-di(tert-butyl)phenyl, 4,4'-biphenyl and 3,5-di(phenyl)phenyl. $R^2$ is particularly preferably phenyl, 1-naphthyl, 4-tert-butylphenyl or 3,5-di(tert-butyl)phenyl.

Y is $OR^6$, where $R^6$ is a linear, branched or cyclic $C_1$–$C_{10}$-alkyl radical, for example methyl, ethyl, n-propyl, isopropyl, n-butyl, sec-butyl, isobutyl, n-pentyl, cyclopentyl, n-hexyl, cyclohexyl, n-heptyl, n-octyl or n-decyl. $R^6$ is preferably methyl or ethyl.

Particular preference is given to the process of the present invention in which the compound of the formula (II)

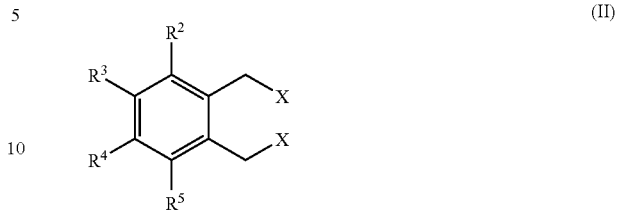

where the radicals X, $R^2$, $R^3$, $R^4$ and $R^5$ are as defined above, is prepared by coupling of a compound of the formula (VI)

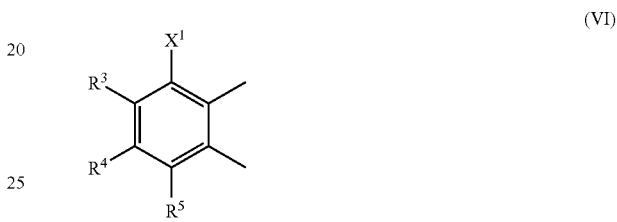

with a compound of the formula (VII)

in the presence of a transition metal catalyst, with either the compound of the formula (VI) or the compound of the formula (VII) firstly being converted into a corresponding organometallic compound, in particular a lithium or Grignard compound, and the coupling product of the formula

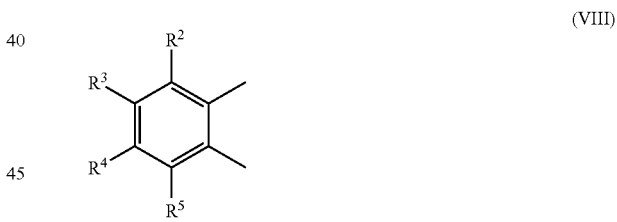

is reacted with a halogenating agent and, if desired, the halogen atoms introduced in this way are subsequently replaced by other halogen atoms, giving the compound of the formula (II)

where $X^1$ is halogen, in particular chlorine, bromine or iodine, preferably chlorine, and $X^2$ is halogen, in particular chlorine, bromine or iodine, preferably bromine.

Compounds of the formulae (VI) and (VII) are commercially available. The compounds of the formula (VI) or (VII) can be converted into the corresponding organolithium compounds or Grignard compounds by methods known from the literature, or the organometallic compounds are in some cases also commercially available. The synthesis of such Grignard reagents is described, for example, in Holm, Torkil, J. Chem. Soc. Perkin Trans. 2.1981, 464–467. The synthesis of further organometallic reagents starting from the compounds of the formulae (VI) and (VII) can be carried out by standard methods of organometallic chemistry which may be found, for example, in March, Advanced Organic Chemistry, 4th edition, 1992, and in the references cited therein.

The aryl-aryl coupling in the presence of a transition metal catalyst for the purpose of synthesizing the compound of the formula (VIII) is known and can be carried out by methods known from the literature, as described, for example, in Synthesis 1990, 147–148. The transition metal catalysts preferably used in the coupling reaction are thus also known from the literature and are generally commercially available.

As transition metal catalysts, it is in principle possible to use transition metal complexes of groups 8 to 10 of the Periodic Table of the Elements, in particular group 10. Particularly useful catalysts are complexes of nickel or of palladium, in particular complexes of nickel, for example nickel(II) chloride, [1,3-bis(diphenylphosphino)propane] nickel(II) chloride ($NiCl_2[dppp]_2$), [1,2-bis(diphenylphosphino)ethane]nickel(II) chloride ($NiCl_2[dppe]_2$), bis(triphenylphosphine)nickel(II) chloride, [1,1'-bis(diphenylphosphino)ferrocene]nickel(II) chloride.methylene chloride adduct. In the case of an arylboronic acid being used in the coupling reaction instead of an aryllithium or arylmagnesium compound, particular preference is given to using palladium complexes as described in WO 98/40331 and the references cited therein as catalysts.

The coupling reaction for preparing the compound of the formula (VIII) is carried out in suitable inert solvents or solvent mixtures appropriate to the particular reactants, for example diethyl ether, tetrahydrofuran, toluene, etc., under a protective gas atmosphere.

The conversion of the two methyl groups in the compounds of the formula (VIII) into two halomethyl groups (formula (II)) is in principle known from the literature and is usually carried out by free-radical side chain halogenation using brominating agents such as elemental bromine or N-bromosuccinimide or using chlorinating reagents such as elemental chlorine or sulfuryl chloride (cf. March, Advanced Organic Chemistry, 4th edition, 1992, and the references cited therein).

The replacement of the halogen radicals X in compounds of the formula (II) by other halogen radicals X is likewise a method known from the literature and is described, for example, in March, Advanced Organic Chemistry, 4th edition, 1992, and the references cited therein.

The preparation of the compound of the formula (III) can be carried out by methods based on procedures known from the literature, as described in Organometallics 1993, 12, 4398. Apart from magnesium in the form of turnings or powder, which may, if appropriate, be corroded on the surface, i.e. activated, by means of 1,2-dibromoethane, it is also possible to use other high-activity magnesium sources such as magnesium-anthracene to produce the compounds of the formula (III) from the compounds of the formula (II).

The reaction of the compound of the formula (III) with compounds of the formula (IV) to form compounds of the formula (V) is in principle a method known from the literature and can be carried out using procedures based on those in Organometallics 1993, 12, 4398 or Organometallics 1999, 18, 4147–4155. The indan-2-ol formed can be dehydrated by standard methods, for example as described in U.S. Pat. No. 5,770,753, to form the indene of the formula (I) or (Ia). As acid catalysts, it is possible to use, for example, p-toluenesulfonic acid, sulfuric acid, hydrochloric acid or a strong acid ion exchanger.

The invention is illustrated by the following nonrestrictive examples:

General Procedures:

The preparation and handling of organometallic compounds was, unless indicated otherwise, carried out with exclusion of air and moisture under argon as protective gas (Schlenk technique or glove box). All anhydrous solvents required were purged with argon and dried over molecular sieves before use. The $^1H$ NMR spectra were measured at 400 MHz in $CDCl_3$. Chromatographic purifications were carried out using Fluka Silica 60 (230–400 mesh).

EXAMPLE 1

4-tert-Butyl-2',3'-dimethylbiphenyl 23.8 g (1.1 eq.) of magnesium (for Grignard reactions from Aldrich) were suspended in 95 ml of tetrahydrofuran (THF) and activated by addition of a small amount of iodine. 62.7 g (0.45 mol) of 2,3-dimethylchlorobenzene were subsequently added. To start the Grignard reaction, a few drops of 1,2-dibromoethane were carefully added. After the reaction had been started successfully, the remaining 62.7 g (0.45 mol) of 2,3-dimethylchlorobenzene diluted with 380 ml of THF were added dropwise at such a rate that the reaction solution boiled gently. The reaction mixture was subsequently refluxed until the magnesium had mostly reacted (2 hours). After the reaction mixture had cooled to room temperature, a further 95 ml of THF were added to the viscous mixture. 190.0 g (0.89 mol) of p-tert-butylbromobenzene diluted with 190 ml of THF were placed in a further reaction flask. 1.0 g (1 mol %) of nickel(II) chloride was added thereto, followed by careful addition of the Grignard solution. The temperature rose briefly to 80° C. The reaction mixture was stirred at 50–55° C. for 2 hours. After cooling to room temperature, 190 ml of 2 molar hydrochloric acid were carefully added. The aqueous phase was extracted with diethyl ether (3×200 ml), the combined organic phases were dried over magnesium sulfate and the solvent was removed under reduced pressure. The residue was recrystallized from boiling ethanol and two crystal fractions were obtained (1st fraction: 139.3 g, 100% according to GC/2nd fraction: 20.5 g, 96.2% according to GC). Combined yield: 159.8 g (0.67 mol/75%). $^1H$ NMR (400 MHz, $CDCl_3$): δ=7.41 ("d", 2H, aromatic), 7.21 ("d"<2H, aromat.), 7.14–7.07 (m, 3H, aromat.), 2.33 (s, 3H, $CH_3$), 2.16 (s, 3H, $CH_3$), 1.36 (s, 9H, tert-butyl) ppm.

EXAMPLE 2

4-tert-Butyl-2',3'-bis(bromomethyl)biphenyl 137.2 g (0.58 mol) of 4-tert-butyl-2',3'-dimethylbiphenyl were dissolved in 576 ml of carbon tetrachloride. 205.1 g (1.15 mol) of N-bromosuccinimide and 1.37 g (8.3 mmol) of AIBN were added and the mixture was heated quickly to reflux temperature. After the reaction was complete (3 hours according to thin layer chromatography), the reaction mixture was cooled to room temperature and the succinimide which precipitated was removed by filtration. The filter cake was washed with further carbon tetrachloride. The combined filtrates were evaporated under reduced pressure to remove the solvent. 259.5 g of crude product were obtained. 550 ml of ethanol were added and the mixture was allowed to stand overnight to crystallize. Since no crystals had precipitated, a small crystal of the product from a previous experiment was added to the solution. The product crystallized out rapidly, and the crystals were separated off by filtration and washed with ethanol.

Yield: 179.8 g (0.45 mol/79%/84.4% by GC). $^1$H NMR (400 MHz, CDCl$_3$): δ=7.45, 7.38, 7.31, 7.21 (4×m, 7H, aromat.), 4.78, 4.61 (2×s, 2×2H, CH$_2$Br), 1.36 (s, 9H, tert-butyl) ppm.

EXAMPLE 3

4-tert-Butyl-2',3'-bis(chloromethyl)biphenyl 40.0 g (101.0 mmol) of tert-butyl-2,3-bis(bromomethyl) biphenyl were dissolved in 660 ml of DMF. 25.7 g (6 eq.) of lithium chloride were added and the reaction mixture was stirred at room temperature for 24 hours. 500 ml of water and 300 ml of diethyl ether were subsequently added and the aqueous phase was extracted with diethyl ether (2×200 ml). The combined organic phases were washed with water (3×150 ml) and saturated sodium chloride solution (1×100 ml) and dried over magnesium sulfate. The solvent was removed under reduced pressure to give a yellow oil. Crystallization from 200 ml of ethanol gave 17.9 g of white crystals. The mother liquor was concentrated under reduced pressure and left to crystallize. A further 5.5 g of a 2nd crystal fraction were obtained. Combined yield: 23.4 g (76 mmol/75%/89.5% by GC). $^1$H NMR (400 MHz, CDCl$_3$): δ=7.46–7.26 (m, 7H, aromat.), 4.86, 4.67 (2×s, 2×2H, CH$_2$Cl), 1.36 (s, 9H, tert-butyl).

EXAMPLE 4

4-(4-tert-Butylphenyl)-2-methyl-1H-indene and 7-(4-tert-butylphenyl)-2-methyl-1H-indene 8.4 g (20.0 mmol) of magnesium-anthracene 3 THF were dissolved in 100 ml of THF. A solution of 3.07 g (10.0 mmol) of tert-butyl-2,3-bis(chloromethyl)biphenyl in 20 ml of THF were added dropwise at 0° C. over a period of 30 minutes. The reaction mixture was stirred at room temperature for another 30 minutes. A sample was taken and hydrolyzed (GC analysis: 60% formation of the bis-Grignard+formation of oligomers). A solution of 741 mg (1 eq.) of methyl acetate in 30 ml of THF was added dropwise at 0° C. over a period of 30 minutes and the reaction mixture was stirred overnight at room temperature. The reaction mixture was subsequently added to a saturated solution of ammonium chloride. The aqueous phase was extracted with diethyl ether (3×100 ml). The combined organic phases were dried over magnesium chloride and the solvent was evaporated under reduced pressure. GC analysis of the crude product (7.28 g) showed 15% of the desired indanol together with anthracene and further by-products. Anthracene was removed by column chromatography using heptane as eluant, and the indanol was eluted using a 1:1 mixture of methylene chloride/ethanol. The yellow oil obtained after removal of the solvents (2.3 g, 64.4% of indanol according to GC) was dissolved in 40 ml of toluene and refluxed in the presence of 5 mol % of p-toluenesulfonic acid for 1.5 hours on a water separator. The organic phase was washed with saturated sodium hydrogen carbonate solution (1×40 ml) and dried over magnesium sulfate. Removal of the solvent and purification by column chromatography gave 0.72 g (2.8 mmol/28%) of a 1:1 mixture of the desired indenes (93% by GC). $^1$H NMR (400 MHz, CDCl$_3$): δ=7.48–7.14 (m, aromat.), 6.72, 6.54 (2×s, =C—H), 3.42, 3.38 (2×s, CH$_3$), 2.16 ("s", CH$_2$), 1.39 ("s", tert-butyl) ppm.

EXAMPLE 5

4-(4-tert-butylphenyl)-2-methylindan-2-ol 633 mg (26 mmol, 4 eq.) of Mg powder (50 mesh/ Aldrich) were dried under reduced pressure with the aid of a hair dryer. 10 ml of THF and 10 drops of 1,2-dibromoethane were added. The mixture was heated to reflux until gas evolution took place and the activation was complete. The solvent was removed under reduced pressure and 10 ml of fresh THF were added. A solution of 2.0 g (6.5 mmol) of tert-butyl-2,3-bis(chloromethyl)biphenyl in 120 ml of THF was added and the suspension was stirred vigorously at room temperature for 3 hours. Stirring was continued overnight and the slightly greenish turbid solution obtained was filtered to remove excess magnesium. The filtrate was cooled to −78° C. and a solution of 482 mg (6.51 mol) of methyl acetate in 60 ml of THF was added dropwise over a period of 1 hour. The reaction solution was warmed to 0° C. over a period of 2 hours. 80 ml of water were subsequently added and the solution was concentrated under reduced pressure. To dissolve the magnesium salts, 3 ml of concentrated hydrochloric acid were added and the aqueous phase was extracted with methylene chloride (3×50 ml). The combined organic phases were dried over magnesium sulfate, and the solvent was subsequently removed under reduced pressure. The product was purified by column chromatography, with the nonpolar by-products being separated off using a heptane/dichloromethane mixture and the product being eluted with pure dichloromethane, giving a yellow product. Yield: 0.64 g (2.28 mmol/35%/94.5% by GC). $^1$H NMR (400 MHz, CDCl$_3$): δ=7.43–7.22 (m, 7H, aromat.), 3.08 (m, 4H, CH$_2$), 1.48 (s, 3H, CH$_3$), 1.35 (s, 9H, tert-butyl) ppm.

EXAMPLE 6

4-(4-tert-butylphenyl)-2-isopropylindan-2-ol 633 mg (26 mmol, 4 eq.) of Mg powder (50 mesh/ Aldrich) were dried under reduced pressure with the aid of a hair dryer. 10 ml of THF and 10 drops of 1,2-dibromoethane were added. The mixture was heated to reflux until gas evolution took place and the activation was complete. The solvent was removed under reduced pressure and 10 ml of fresh THF were added. A solution of 2.0 g (6.5 mmol) of tert-butyl-2,3-bis(chloromethyl)biphenyl in 120 ml of THF was added and the suspension was stirred vigorously at room temperature for 3 hours. Stirring was continued overnight and the slightly greenish turbid solution obtained was filtered to remove excess magnesium. The filtrate was cooled to −78° C. and a solution of 665 mg (6.51 mol) of methyl isobutyrate in 60 ml of THF was added dropwise over a period of 1 hour. The reaction solution was warmed to 0° C. over a period of 2 hours. 80 ml of water were subsequently added and the solution was concentrated under reduced pressure. To dissolve the magnesium salts, 3 ml of concentrated hydrochloric acid were added and the aqueous phase was extracted with methylene chloride (3×50 ml). The combined organic phases were dried over magnesium sulfate, and the solvent was subsequently removed under reduced pressure. The product was purified by column chromatography, with the nonpolar by-products being separated off using a heptane/dichloromethane mixture and the product being eluted with pure dichloromethane, giving a yellow product. Yield: 0.66 g (2.14 mmol/33% 96% by GC).
$^1$H NMR (400 MHz, CDCl$_3$): δ=7.41–7.21 (m, 7H, aromat.), 3.18–2.91 (m, 4H, CH$_2$), 1.92 (m, 1H, CH), 1.36 (s, 9H, tert-butyl), 1.02 (t, 6H, CH$_3$) ppm.

The invention claimed is:
1. A process for preparing substituted indenes of the formula (I)

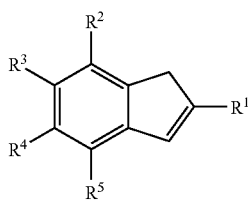

(I)

and their double bond isomers of the formula (Ia)

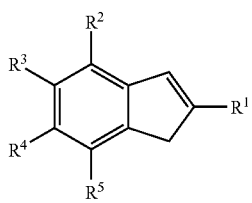

(Ia)

which comprises converting a compound of the formula (II)

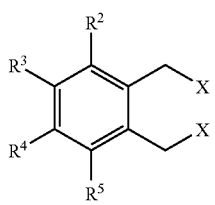

(II)

into a bisorganometallic compound of the formula (III)

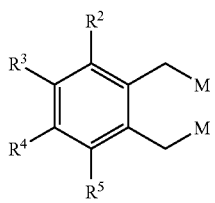

(III)

and reacting this with a compound of the formula (IV)

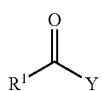

(IV)

to give an indanol of the formula (V)

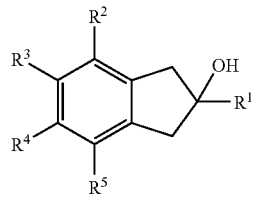

(V)

and converting this into an indene of the formula (I) or (Ia) by elimination of water, wherein the compound of the formula (II)

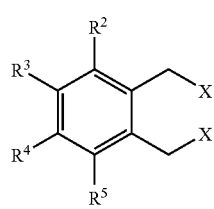

(II)

is prepared by coupling of a compound of the formula (VI)

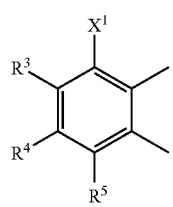

(VI)

with a compound of the formula (VII)

R$^2$—X$^2$ (VII)

in the presence of a transition metal catalyst, with either the compound of the formula (VI) or the compound of the formula (VII) firstly being converted into a corresponding organo-metallic compound, and the coupling product of the formula (VIII)

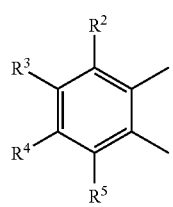

(VIII)

is reacted with a halogenating agent to give a compound of the formula (II), where

- $R^1$ is a linear, branched or cyclic $C_1$–$C_{10}$-alkyl radical,
- $R^2$ is a substituted or unsubstituted $C_6$–$C_{18}$-aryl radical selected from the group consisting of phenyl, 1-naphthyl, phenanthryl, 3-tert-butylphenyl, 4-tert-butylphenyl, 3,5-di(tert-butyl)phenyl, 4,4'-biphenyl and 3,5-di(phenyl)phenyl,
- $R^3$–$R^5$ are each hydrogen,
- X is a chlorine atom,
- $X^1$ is halogen,
- $X^2$ is halogen,
- M is magnesium monochloride and,
- Y is $OR^6$, where $R^6$ is a linear, branched or cyclic $C_1$–$C_{10}$-alkyl radical.

2. A compound of the formula (II)

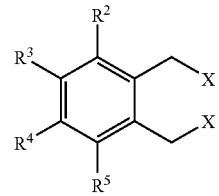

(II)

where $R^2$, $R^3$, $R^4$, $R^5$ and X are defined in claim 1.

3. The process of claim 1 wherein $X^1$ is chlorine, bromine or iodine and $X^2$ is chlorine, bromine or iodine.

4. The process of claim 3 wherein $X^1$ is chlorine and $X^2$ is bromine.

* * * * *